(12) United States Patent
Vardi

(10) Patent No.: US 12,396,671 B2
(45) Date of Patent: Aug. 26, 2025

(54) ECG MONITOR DEVICE WITH ELECTRODE PAD

(71) Applicant: ETROG SYSTEMS LTD., Jerusalem (IL)

(72) Inventor: Eyal Dov Vardi, Bet Nir (IL)

(73) Assignee: ETROG SYSTEMS LTD., Kiryat Gat (IL)

( * ) Notice: Subject to any disclaimer, the term of this patent is extended or adjusted under 35 U.S.C. 154(b) by 0 days.

(21) Appl. No.: 17/139,447

(22) Filed: Dec. 31, 2020

(65) Prior Publication Data

US 2021/0321925 A1 Oct. 21, 2021

Related U.S. Application Data

(60) Provisional application No. 63/011,667, filed on Apr. 17, 2020.

(51) Int. Cl.
| | |
|---|---|
| *A61B 5/00* | (2006.01) |
| *A61B 5/271* | (2021.01) |
| *A61B 5/282* | (2021.01) |
| *A61B 5/346* | (2021.01) |

(52) U.S. Cl.
CPC .............. *A61B 5/282* (2021.01); *A61B 5/271* (2021.01); *A61B 5/346* (2021.01)

(58) Field of Classification Search
None
See application file for complete search history.

(56) References Cited

U.S. PATENT DOCUMENTS

| | | | |
|---|---|---|---|
| 5,307,818 A | 5/1994 | Segalowitz | |
| 2008/0009694 A1* | 1/2008 | Hopman | A61B 5/25 600/374 |
| 2008/0281180 A1* | 11/2008 | Choe | A61N 1/0408 600/391 |
| 2013/0281814 A1* | 10/2013 | Tilt | A61B 5/282 600/382 |
| 2014/0066797 A1* | 3/2014 | Lisogurski | A61B 5/349 600/513 |
| 2015/0374251 A1* | 12/2015 | Yoshioka | A61B 5/30 600/386 |
| 2018/0317783 A1 | 11/2018 | Petrikovsky et al. | |
| 2018/0353107 A1* | 12/2018 | Xu | A61B 5/369 |
| 2019/0030352 A1* | 1/2019 | Sullivan | A61N 1/3987 |
| 2020/0000355 A1* | 1/2020 | Khair | A61B 5/746 |
| 2020/0289026 A1* | 9/2020 | Bardy | A61B 5/6824 |
| 2020/0326254 A1* | 10/2020 | Azimpour | G06F 3/044 |
| 2021/0228153 A1* | 7/2021 | DeCerce | A61B 5/686 |

FOREIGN PATENT DOCUMENTS

WO WO-2021080369 A1 * 4/2021

OTHER PUBLICATIONS

Extended European Search Report dated Jun. 7, 2022 issued in European Patent Application No. 21218290.1.

\* cited by examiner

*Primary Examiner* — Gary Jackson
*Assistant Examiner* — Anata A Gupta
(74) *Attorney, Agent, or Firm* — Amster, Rothstein & Ebenstein LLP

(57) ABSTRACT

The present invention relates to an ECG monitor device including a removable electrode pad and a monitor element configured for use with a single lead that receives and processes information associated with a plurality of leads.

20 Claims, 8 Drawing Sheets

ECG MONITOR DEVICE WITH ELECTRODE PAD

CROSS-REFERENCE TO RELATED APPLICATIONS

The present application claims benefit of and priority to Provisional Patent Application Ser. No. 63/011,667 filed Apr. 17, 2020 entitled ECG MONITOR DEVICE WITH ELECTRODE PAD, the entire content of which is incorporated by reference herein.

BACKGROUND

Field of the Disclosure

The present disclosure relates to an electrocardiograph (ECG) monitor device that includes a detachable electrode pad configured for use with a single lead and operable to receive data from a plurality of leads and electrodes.

Related Art

Conventional electrocardiograph devices utilize a plurality of electrodes connected to a separate monitoring unit via a plurality of wires to provide data from a plurality of positions on the patient's body. In general, the more electrodes that are used, the more information provided. In general, in order to provide useful information, at least 2 electrodes are provided in a single lead ECG, for example. More commonly, a conventional ECG is referred to as a 12 lead ECG and used 10 electrodes to provide the 12 leads. The individual electrodes are positioned in particular locations to detect small changes in electrical activity of the patient's heart. For example, a conventional 12-lead ECG utilizes ten electrodes placed on the patient's limbs and on the surface of the patient's chest. These electrodes may be used to determine the overall magnitude of the heart's electrical potential based on measurements from twelve different angles ("leads") recorded over a period of time (usually ten seconds) using the electrodes. In this manner, the magnitude and direction of the heart's electrical depolarization is captured at each moment throughout the cardiac cycle.

The electrodes are conductive pads attached to the user's body. Any pair of electrodes measures the electrical potential difference between the two corresponding locations. Each pair of electrodes may form a lead with individual wires attached to each electrode. In addition, "leads" may also be formed between a physical electrode and a virtual electrode, known as the Wilson's central terminal, whose potential is defined as the average potential measured by three limb electrodes that are attached to the right arm, the left arm, and the left foot, respectively. Leads are typically divided into three groups: limb; augmented limb; and precordial or chest. A 12-lead ECG usually has a total of three limb leads and three augmented limb leads arranged like spokes of a wheel in the coronal plane (vertical), and six precordial leads or chest leads that lie on the perpendicular transverse plane (horizontal). Such conventional ECG devices are effective in providing useful data, however, are bulky, difficult to properly apply and complicated to use since they require placement of individual electrodes at specific locations.

Some ECG devices may use a single lead, and thus, are less bulky and easier to use, however, provide less information, and thus, are of less value in identifying heart problems. Further, these single lead devices do not allow for use with multiple leads such that their performance cannot be enhanced.

Accordingly, it would be useful to provide an ECG monitor device that includes a monitor element configured for connection to a single lead that receives and processes data for a plurality of leads and enables generation of a graphical ECG wave report that corresponds to that which would be provided by multiple leads.

SUMMARY

It is an object of the present disclosure to provide an ECG monitor device including an electrode pad connected to a monitor device configured for use with a single lead that receives and processes data to provide ECG information for both a single lead and multiple lead ECG.

Another object of the present disclosure is to provide an electrode pad and monitor device for use as a fetal/maternal heart monitor.

An ECG monitor device in accordance with an embodiment of the present disclosure includes: an ECG monitor element including: a processor; a memory element operatively connected to the at least one processor; a power source; an analog interface operatively connected to the at least one processor; a communication element operatively connected to the processor and the memory element and configured to send and receive data; and an electrode pad connected to the ECG monitor element including: a first group of electrodes positioned on a first portion of the electrode pad and directly connected to the analog interface; a second group of electrodes positioned on a second portion of the electrode pad, where the second portion of the electrode pad is elastic and extends in a continuous strip from one side of the electrode pad; a multiplexer mounted on the electrode pad and connected to the analog interface, wherein the second group of electrodes is connected to the multiplexor and the multiplexor is operable to selectively provide data from each electrode of the second group of electrodes to the ECG monitor element; wherein the processor processes data from the first group of electrodes and the second group of electrodes to provide electrocardiogram information sufficient to selectively provide an ECG waveform consistent with a single lead electrode and a multiple lead ECG.

In embodiments the ECG monitor device includes a connector element electrically connecting the monitor element to the electrode pad.

In embodiments, the connector element is a magnetic element configured to securely connect the monitor element to the electrode pad.

In embodiments, the processor provides control information to the multiplexer associated with sampling of data provided by the second group of electrodes.

In embodiments, the control information indicates a sampling time interval and sampling duration.

In embodiments, the electrode pad includes a pad memory element including identification information associated with a configuration of the electrodes on the electrode pad.

In embodiments, the processor receives the identification from the pad memory and the control information is based on the identification information.

In embodiments, the processor processes data provided from the first group of electrodes and the second group of electrodes to provide the electrocardiogram information.

In embodiments, the processing includes determining electrode input information associated with a respective electrode that provided a first portion of the data.

In embodiments, the processing includes analyzing a time stamp, a sampling interval and a sampling determination to determine the electrode input information.

In embodiments, the electrode input information is stored in the memory and used to construct the ECG waveform.

A method of testing the ECG monitor includes activating the ECG monitor device; receiving, at the ECG monitor element from the electrode pad, test identification information associated with the test to be performed including duration information; determining, by the ECG monitor device, the configuration of the electrode pad; determining, by the ECG monitor device, timing information for data capture of data provided by the electrode pad based at least on the configuration of the electrode pad; receiving, by the ECG monitor device from the electrode pad, first electrode data; determining, by the ECG monitor device, that the first electrode data is valid; wherein, when the first electrode data is invalid, an invalid message is generated and stored in the memory; and otherwise, a valid message is generated and stored in the memory with the first electrode data; determining, by the ECG monitor device, whether valid electrode data has been provided from all electrodes; wherein, when valid data has not been received from all electrodes, the receiving step and determining steps are repeated for second electrode data; and otherwise, a test complete report is generated and saved in memory to indicate that the test has been completed.

In embodiments, the step of determining the configuration of the electrode pad is based on the identification information.

In embodiments, the step of determining the configuration of the electrode pad includes comparing the information to stored identification information included in the memory.

In embodiments, the step of determining the configuration of the electrode pad includes receiving instructions via the communication element.

In embodiments, the timing information is determined based on the configuration of the electrode pad and a number of leads to be used in providing the ECG waveform.

In embodiments, the step of determining that the first electrode data is valid is based on noise to signal ratio of the signal including the first electrode data.

In embodiments, the step of determining that the first electrode data is valid is based on a percentage of detected peaks in the signal including the first electrode data.

In embodiments, the step of determining that the first electrode data is valid is based on an anticipated wave pattern associated with the electrode pad.

In embodiments, the test complete report is transmitted to an administrator computer system using the communication element.

BRIEF DESCRIPTION OF THE DRAWINGS

Exemplary embodiments of the present invention will be described with references to the accompanying figures, wherein.

DETAILED DESCRIPTION OF THE EMBODIMENT

Figure 1:
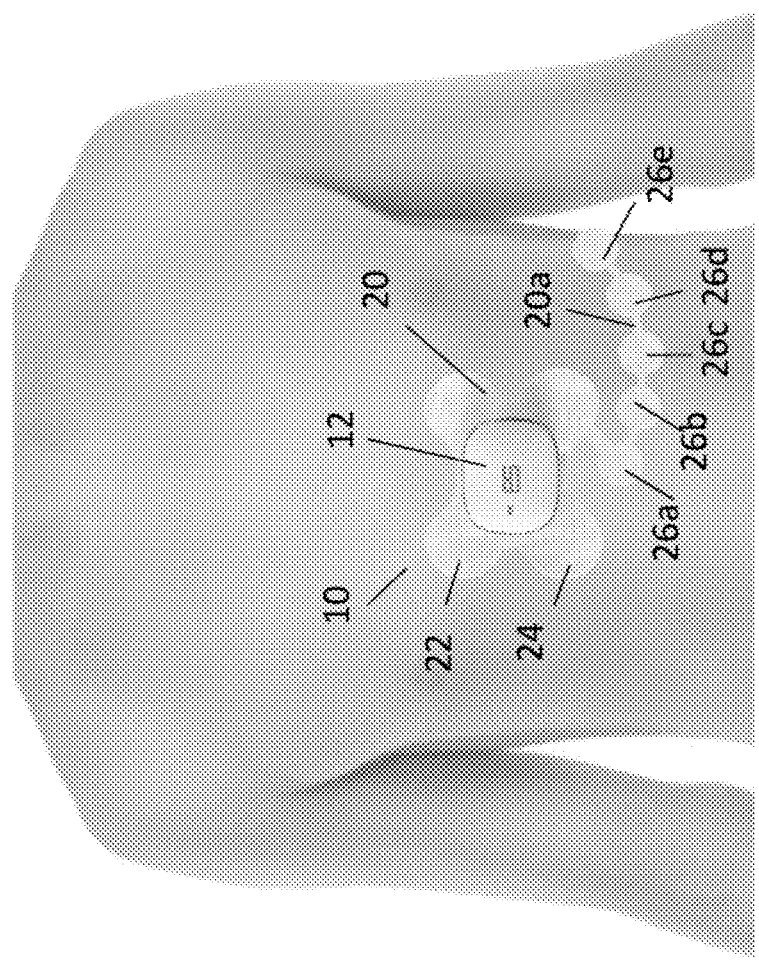
FIG. 1 illustrates an exemplary embodiment of an ECG monitor device including a single lead electrode pad positioned on a user's body in accordance with an embodiment of the present disclosure.
Figure 2:
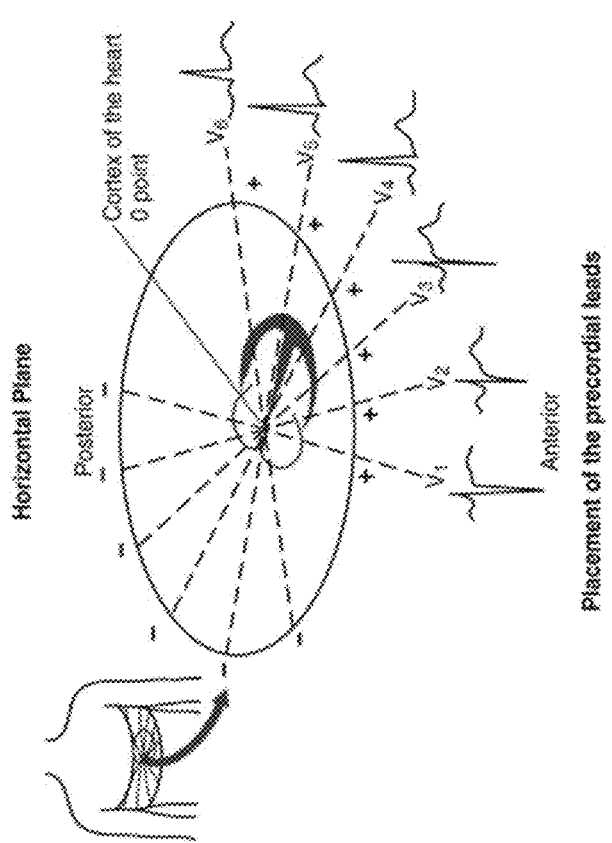
FIG. 2 illustrates a schematic representation of the electrical signals detected by the respective electrode elements of the ECG monitor device of FIG. 1.

FIG. 1 illustrates an ECG monitor device 10 attached to a patient's body. In embodiments, the monitor device 10 includes a monitor element 12 (ES008) connected to an electrode pad 20 that includes a plurality of electrode elements 22, 24 and 26a, 26b, 26c, 26d and 26e. In embodiment, the electrodes 22, 24 and 26a, 26b, 26c, 26d and 26e may provide voltage information associated with a patient's heart at various pints on the patient's body. In embodiments, the monitor element 12 is configured for use to provide a single lead ECG, however, receives and processes information from electrodes 22, 24 and 26a, 26b, 26c, 26d and 26e for both single lead and multiple led electrocardiograms ECGs. In embodiments, the electrode 22 provides the right arm lead (RA) and the electrode 24 provides the right leg lead (RL) and are provided on a base portion of the pad 20. In embodiments, one of the electrodes 26a-e may be considered a third limb electrode, leg or arm. In embodiments, the electrodes 26a, 26b, 26c, 26d and 26e may be positioned on the patient's chest or other locations as may be prescribed by a doctor or designated by another health care professional and provide the chest leads for the ECG. FIG. 2 illustrates exemplary positioning of electrodes for an ECG and ECG waveforms provided using information from the electrodes. In embodiments, the electrodes 26a, 26b, 26c, 26d and 26e may be positioned on a continuous strip 20a extending horizontally across the user's chest. In embodiments, the electrodes 26a, 26b, 26c, 26d and 26e may be spaced apart on the strip 20a sufficiently to provide the chest leads for either a single lead or multiple lead ECG. In embodiments, the spacing between the electrodes may be based on patient physiology and may be determined by a medical professional. In embodiments, the minimum distance between the right arm electrode 22 and each of the electrodes 26a, 26b, 26c, 26d and 26e may be 10 cm. In embodiments, the continuous strip 20a may be made of an elastic material such that it allows for adjustment of the placement of the electrodes 26a, 26b, 26c, 26d and 26e on the user's body. In embodiments, the elastic material may be stretchable to allow for modification of placement of the electrodes 26a, 26b, 26c, 26d and 26e. In embodiments, the particular placement of respective electrodes 26a, 26b, 26c, 26d and 26e may depend on patient physiology. In embodiments, the electrodes 26a, 26b, 26c, 26d and 26e may be positioned in appropriate positions by a clinician. In embodiments, the electrode pad 20 may be provided in different sizes (e.g. S, M, L, XL, to name a few). In embodiments, a length of the continuous strip 20a may be 15 cm, 25 cm, 30 cm or 40 cm, to name a few, to accommodate different body sizes.

Figure 3:
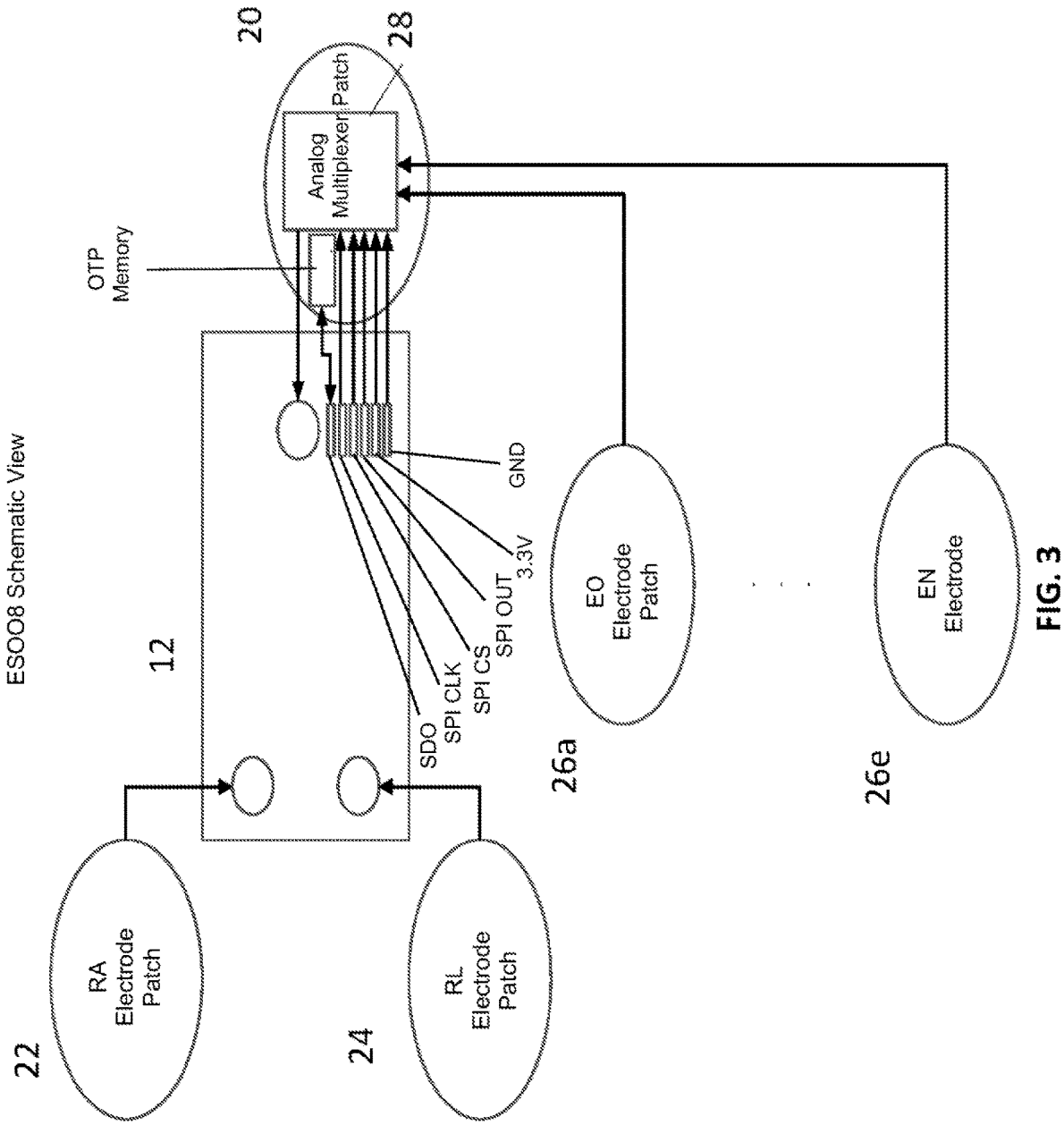
FIG. 3 illustrates a schematic representation of the electrode pad and its connection to the monitor device in accordance with an embodiment of the present disclosure.
Figure 4:
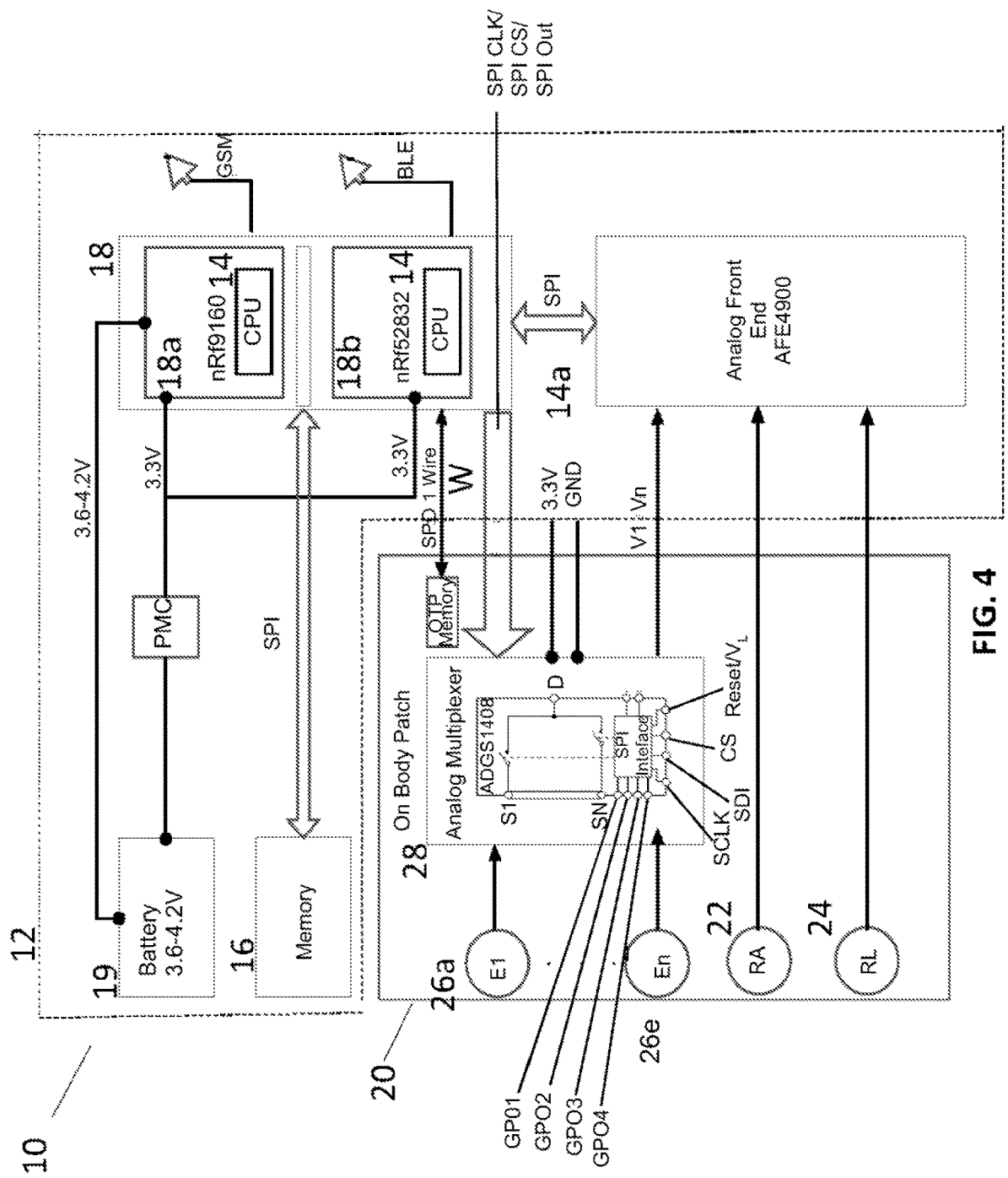
FIG. 4 illustrates a block diagram of the ECG monitor device of FIGS. 1 and 3 in accordance with an embodiment of the present disclosure.

In embodiments, the electrode pad 20 may include an analog multiplexer 28 (see FIGS. 3-4) that may be connected to the electrodes 26a, 26b, 26c, 26d and 26e. In embodiments, the analog multiplexer 28 may also be connected to the monitor element 12 (see FIGS. 3 and 4, for example). In embodiments, the multiplexer 28 receives data from the electrodes 26a, 26b, 26c, 26d and 26e and provides a single output to the monitor element 12 to provide data to the monitor element 12. In embodiments, the multiplexer 28 may also receive information from the monitor element 12. In embodiments, the monitor element 12 may include output pins or ports to provide information to the multiplexer 28 with respect to determining which input associated with which electrode of the electrodes 26a, 26b, 26c, 26d and 26e to sample data from as well as a period of time during which the selected electrode is sampled and a time interval at which sampling will begin. In embodiments, as can be seen in FIGS. 3-4, for example, these output ports may include a clock output (serial peripheral interface (SPI) CLK), a control data output (SPI CS), a data output (SPI OUT), a power output (3.3V) and a ground output (GND). In embodiments, the control data output may be connected to the pad 20, or to the multiplexor 28 to provide instructions with respect to the sampling of electrode data. In embodiments, this connection may be a wired connection between the monitor element 12 and the pad 20. In embodiments, the output port may be used to output the ECG information or other information. In embodiments, a battery 19 or other portable power supply may be provided in the monitor element 12 and may provide power to the monitor element 12 as well as the multiplexer 28 of the pad 20. In embodiments, power and ground may be provided for the multiplexer 28 via a separate source, if desired. In embodiment, the monitor element 12 may include analog interface 14a (AFE 4900) that is connected to and receives information from the electrodes 22, 24 as well as the multiplexor 28 and may provide it to CPU 14 or another processor included in the monitor device 12.

In embodiments, the electrodes 26a, 26b, 26c, 26d and 26e may provide data regarding the depolarization of the patient's heart to the multiplexer 28. In embodiments, the multiplexer 28 may receive the data from the multiple electrodes 26a, 26b, 26c, 26d and 26e via a single connection and may provide the data to the monitor element 12 via the analog interface 14a, for example.

In embodiments, the monitor element 12 may include a bidirectional communication device 18 and may provide data to and receive data and instructions from an administrator system or a central control platform (not shown). In embodiments, communication may take place via the Internet and may include additional devices that may be connected to or included in the administrator system or central control platform. In embodiments, the bidirectional communication device 18 may be a wireless communication device, which may use GSM or BLE communication, to name a few. In embodiments, the monitor element 12 may monitor other information related to the patient as well, including temperature and blood pressure to name a few. In embodiments, the monitor element 12 may include one or more processors, which may be or may be included in a CPU 14 and one or more memory elements 16. In embodiments, the CPU 14 may be provided as part of the GSM module 18a or the BLE module 18b in the bidirectional communication device 18, as illustrated in FIG. 4, for example. The one or more memory elements 16 may store processor executable code that, when executed by the CPU 14, may be used to provide electrocardiogram data based on the data provided by the electrodes that may be used to render an electrocardiogram based on information provided by electrodes of the electrode pad 20. In embodiments, the electrocardiogram information may be stored in the one or more memory elements 16 or may be transmitted using the bidirectional communication device 18 to an administrator or a central monitoring platform or system. Co-Pending U.S. patent application Ser. No. 16/356,680 filed Mar. 18, 2019 entitled SYSTEM AND METHOD FOR REMOTE MONITORING OF A USER'S VITAL SIGNS AND BODILY FUNCTIONS discloses a wearable monitoring device suitable for use as the monitoring element 12 and applicant hereby incorporates by reference the entire content of this application into the present application. In embodiments, the monitor element 12 may communication with a smart phone or other mobile electronic device and may send ECG information to and receive instructions from the mobile electronic device. In embodiments, the electrocardiogram information may be provided to the mobile used device and displayed on a display thereof.

In embodiments, the processor 14 (CPU) may control the analog front end (analog interface) 14a (AFE) which captures data used to provide the leads and has 3 inputs to receive data. In embodiments, as can be seen in FIGS. 3-4, for example, the electrodes 22 (RA) and 24 (RL), respectively, may be directly connected to the analog front end 14a. These electrodes 22 (RA) and 24 (RL) may be considered a first group of electrodes and are used to provide the limb leads. In embodiments, as indicated in FIG. 4, the analog front end 14a may be provided in the monitor element 12. In embodiments, the other electrodes 26a, 26b, 26c, 26d and 26e, may be considered a second group of electrodes and are positioned on the elastic strip 20a and may be connected to the multiplexer 28 discussed above which is in turn connected the to the analog front end 14a. In embodiments, the multiplexer 28 may be mounted in the monitor element 12. It is noted that additional or fewer electrodes may be provided among this second group of electrodes to provide the chest leads (or other leads) depending on what type of ECG is being implemented. In general, in order to obtain useful ECG data three electrodes are used to provide for a single lead ECG, which may include the electrodes 22, 24. In order to provide additional leads, additional electrodes may be used and provided is desired position. In embodiments, all of the electrodes used in conjunction with the monitor element 12 are positioned in the torso area of the body, while their specific placement may vary based on physiology as noted above. In embodiments, the memory element 16 may include executable instructions to implement ECGs using different numbers of leads. That is, the memory element 16 may include executable instructions to process data provided by the electrodes to provide for single lead ECGs or multiple lease ECGs.

In embodiments, the patch or pad 20 may include various configurations and numbers of electrodes. In embodiments, each configuration may be used for a different application. For example, standard one lead ECG data may be used to monitor and detect heart arrhythmias. In embodiments, four lead ECG data or 12 lead ECG data may be used to detect arterial fibrillation or myocardial infarction. In embodiments, the same pad 20 may provide the one lead ECG data, the four lead ECG data and the 12 lead ECG data via the multiplexer 28 which may samples the data provided by the electrodes 22a-22e differently depending on whether a single lead ECG, a 4 lead ECG or 12 lead ECG is to be provided. In embodiments, the patch 20 may include a sufficient number electrodes to provide single lead ECG information, four lead ECG information and 12 lead or more ECG information. In embodiments, regardless of the configuration, the electrodes will provide data to the monitor element 12 and this information may be analyzed by the monitor element 12 based on the position of the respective electrodes providing the data as collected via the multiplexer 28.

In embodiments, a detection or test procedure may be implemented upon initialization of the ECG monitor device 10 to test what type (configuration) of electrode pad 20 is connected to the monitor element 12 and the number of electrodes included in the pad. In embodiments, this may be accomplished using a single wire control connection W to a one-time programmable (OTP) memory module on the pad 20. In embodiments, analysis of the data provided by the electrode pad 20 may be analyzed to determine the current configuration of the electrodes. In embodiments, the test may retrieve identification information that may be used by the CPU 14, which may include a security authentication code that identifies the pad 20 as being genuine. In embodiments, the identification information may be a serial number, for example). In embodiments, each of the electrode pads 20 may be uniquely identified. In embodiments, unique identification information, which may include the security authentication code, may be generated or assigned during manufacturing. In embodiments, the unique identification information may be used to identify or indicate the unique capabilities or characteristics of the respective electrode pad 20.

Figure 7:
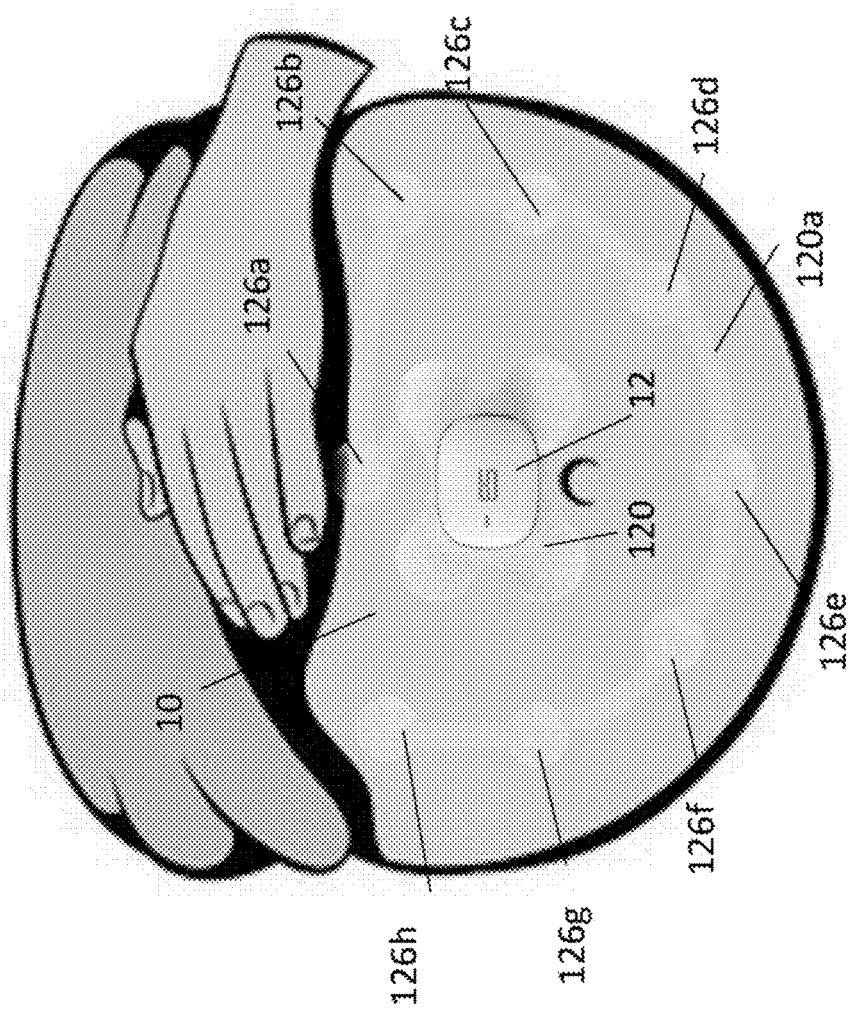
FIG. 7 illustrates an ECG monitoring system including a monitor device and a single lead electrode pad positioned on a user's body to detect electrical activity associate with a fetal heart in accordance with an embodiment of the present disclosure.

In embodiments, identification information may be stored in the memory 16, for example, or another memory element operatively connected to or in communication with the monitor device 12 to identify and/or authenticate the electrode pad 20. In embodiments, an authentication algorithm may be executed by or on behalf of the monitor element 12 in order to identify or authenticate the electrode pad. In embodiments, the unique identification information may be analyzed remotely or otherwise, and may be compared to data stored in an authorization database. In embodiments, this information may identify the type of pad 20 connected to the monitor element 12, for example, a single or multiple lead ECG pad 20 as shown in FIG. 1, a fetal heartbeat pad 120 as illustrated in FIG. 7, or another type of pad. In embodiments, the electrode patch or pad 20 may be provided in any other forms, for example, including additional leads and electrodes. As noted above, in embodiments, the electrode pad 20 may be configured to provide one lead ECG data, four lead ECG data or 12 lead data. In embodiments, the electrode pad 20 may be used to provide ECG data to provide for other multiple lead configurations.

In embodiments, the electrode pad 20 may be configured for use on patients that are not human. Accessing the unique identification information associated with the pad 20 may provide an identification of the type of pad 20 and thus how the data provided should be processed. This information may also provide information indicating the number of electrodes available on the pad 20. In embodiments, the unique identification information may be stored in the OTP, which may be a 64-bit ROM that includes a unique 48-bit serial number, an 8-bit CRC, and an 8-bit family code (01h).

In embodiments, other configurations may be used for the OTP. In embodiments, data may be transferred serially through the control wire W. As noted above, the unique identification information may be used as an indication of the number of electrodes on the pad, the size of the pad (S, M, L, X, etc.), manufacturing date, batch no and security number, to name a few. In embodiments, a communication protocol may be used to communicate between the CPU 14 and the OTP via the wire W. In embodiments, an authentication test may be conducted every time the device 10 is initiated and detects "LEADS ON BODY" prior to the start of capturing data (see FIG. 5 for example). In embodiments, the test need not be repeated provided that the device 10 is connected to the patient's body continuously. In embodiment, the monitor element 12 may be connected to the pad 20 via a magnetic conductive connection element to maintain a secure connection. In embodiments, the connection element may have a unique configuration suitable for connection to the monitor device 12. In embodiments, the connection element may have a unique configuration suitable for connection to the OTP.

In embodiments, once the test is complete, the CPU 14 may initiate the ECG test by providing instructions to capture data from the electrodes using the AFE 14a. In embodiments, this may include setting the relevant timing of the input from the electrodes 26a, 26b, 26c, 26d and 26e, selectively such that data from the electrodes is sampled at a desired time and for a desired time period. It is noted that this process may vary depending on the number of electrodes included in the pad 20 and the configuration of the pad. In embodiments, the ECG data provided by the pad 20 will provide for a near real time view of the ECG data from multiple leads simultaneously since all of the electrodes 26a, 26b, 26c, 26d and 26e collect data from different positions continuously. The ECG data is provided to the monitor element 12 and sampled as desired via multiplexer 28, for example. In embodiments, the sampling may occur at a 50 micro second intervals. In embodiments, the sampling interval may be higher or lower. In embodiments, the continuous transmission of information from the electrodes to the monitor element 12 allows for near real time construction of the ECG waveform in which any small gaps in data will be on the order of microseconds and thus generally unnoticed by observers using their eyes. In embodiments, the CPU 14 may be provided with the appropriate timing information based on the unique identification information provided from the OTP during the test. In embodiments, the CPU 14 may include instructions to specify timers for a length of every signal capture time. In one example, the timing may be set such that the electrode data capture changes every 3 seconds. In embodiments, this timing may be varied.

In embodiments, the data captured from each electrode may be stored in an internal memory, such as the memory element 16 and may be encoded with a time stamp and electrode input information to specify the source electrode. In embodiments, since the sampling rate and the start time are known, the electrode input information may be determined. In embodiments, the electrode input information may include an electrode number indicating the source electrode. In embodiments, the electrode input information may include the ECG data capture (voltage information provided at the source electrode) which may be used to determine the location of the source electrode and may be used to provide the ECG waveform. In embodiments, the encoded and stamped stored data may be provided to a display and reporting program, which may be provided by or through an administrator system or other central reporting platform that may use the data to recreate a viewable ECG waveform that is comparable to a multiple lead ECG reading at a display provided at or in communication with the administrator system, central reporting platform or mobile electronic device, to name a few. In embodiments, the administrator system may be provided locally, within view of the patient or a care provider treating the patient manually and/or may be remote. In embodiments, the encoded and stamped stored data may be provided to a mobile electronic device, either locally or remotely as well. In embodiments, the mobile electronic device may be or be in communication with the administrator system. In embodiments, the ECG waveform may be displayed on a display of the mobile electronic device and or at the administrator system. In embodiments, such a waveform may be used by a health professional to determine possible heart conditions. In embodiments, the results may indicate that further examination using multiple leads may be warranted proper assessment of Coronary Heart Disease (CHD), myocardial infarction (MI) and more.

Figure 5:
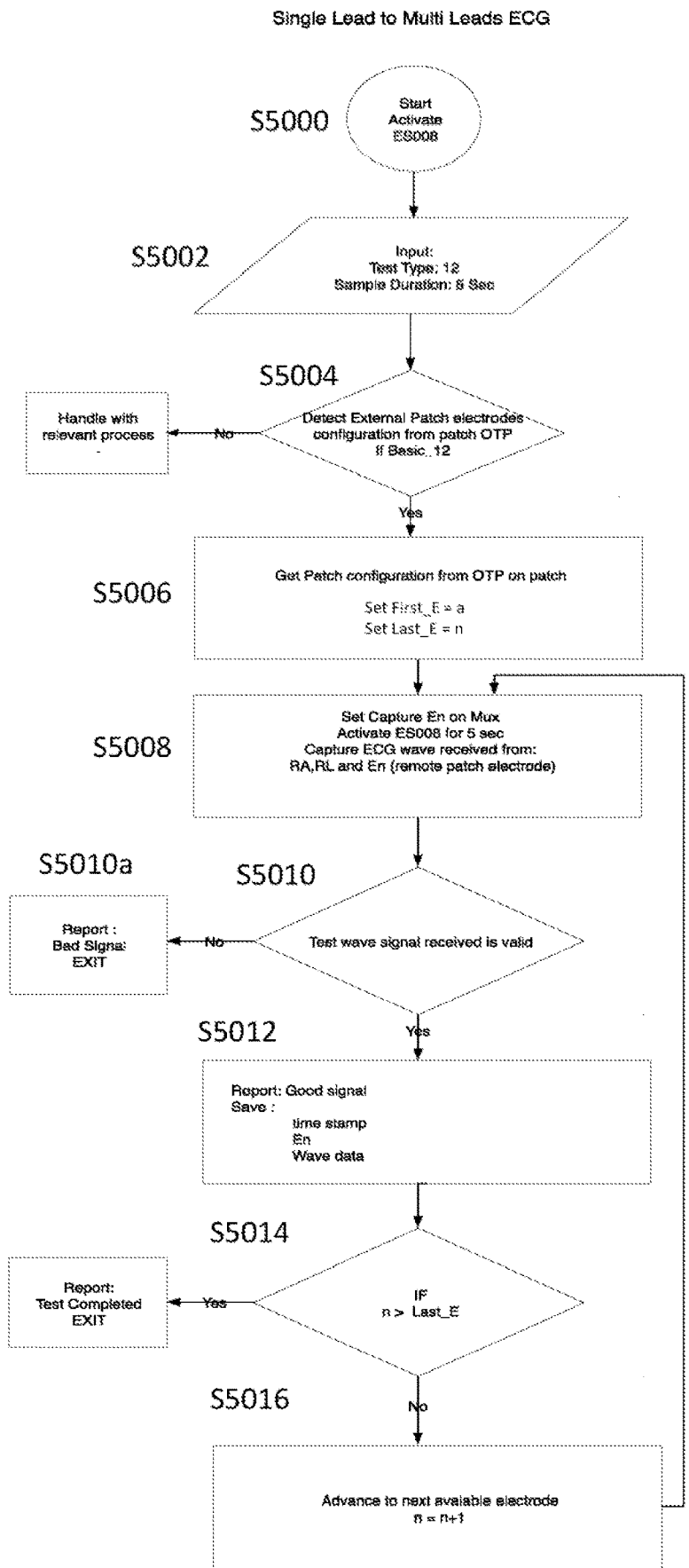
FIG. 5 illustrates an exemplary flow chart showing a method of providing an ECG using the monitor device of FIG. 1 in accordance with an embodiment of the present disclosure.

FIG. 5 illustrates an exemplary flow chart showing a method of testing the monitor device 10 of the present disclosure. At step S5000, the method begins by activating the monitor element 12 (ES008). In embodiments, the monitor element 12 may be activated based on a timer, based on instructions provided via wireless transmission or via activation of an input button or switch on the monitor device 10. In embodiments, at step S5002, the test discussed above may be initiated. That is, at step S5002, test type data may be received by the monitor device indicating a type of test to be conducted. In embodiments, the test type information may be provided by user, i.e. a patient or a clinician. In embodiments, the test type data may be provided by the administrator system. In embodiments, the test type data indicates the test type, the duration of each recording cycle may be indicated. As noted above, this identification data may be uniquely associated with the particular pad 20. In embodiments, in step S5004, a configuration of the electrode pad 20 may be determined by the monitor element 12, based on the identification information, for example. In embodiments, if the configuration is not determined (NO at step S5004) the step may be repeated. In embodiments, if the configuration is not determined, the test may be canceled and an error message may be provided. In embodiments, if the configuration is not determined, this may be an indication that the electrode pad 20 is not compatible with the monitor element 12. In embodiments, the test may be performed after the monitor 12 and pad 20 are placed on the patient. Provided that that the pad remains in place, typically, the test will not be run again. In embodiments, the test may be run periodically, or aperiodically to confirm that the pad 20 has not moved. Otherwise, in embodiments, at step S5006, identification information associated with the pad 20 may be retrieved from the OTP on the pad 20. In embodiments, the identification information may include identification information associated with each of the electrodes 22, 24, 26a, 26b, 26c, 26d and 26e. In embodiments, the identification information includes a first electrode ID information ("First_E=a") and last electrode ID information (Last_E=n") which may be used to identify the start and end cycle for the electrodes. For a test associated with a 12 lead ECG, for example, the cycle may be 5 s. In embodiments, at step S5008, timing information for the data capture from the electrodes may be set and data may be received from the electrodes based on the timing. As noted above, in embodiments, this timing information may be based on the identification information received from the OTP or provided from the administrator or another computer system. In embodiments, at step S5010, a determination may be made as to whether the data received during the timing period is valid. In embodiments, this determination may be made by the monitor element 12. In embodiments, in this step, an algorithm may be used to test signal quality based on NSR (noise to signal ratio), percentage of detected peaks and anticipated wave pattern for the specific pad 20. If not, at step S5010a, a report indicating an invalid signal may be generated and provided to the administrator system, for example. In embodiments, the report may be provided to the mobile electronic device. Otherwise, in embodiments, at step S5012, a report indicating a good signal and the received data may be generated and provided to the administrator system, for example, or to a display and reporting program that may be associated with or provided by the administrator system, for example. In embodiments, the data may also be saved in the memory 16 discussed above and used to create the waveform. In embodiment, the data or portions thereof may be displayed on the display of the mobile electronic device. At step S5014, in embodiments, a determination may be made as to whether a valid data signal has been received from all electrodes on the pad 20. If so, in embodiments, at step S5014a, a report may be generated and provided to the administrator system, for example, to indicate that the ECG test is complete. In embodiments, this report may be stored in the memory 16 and may be sent to the administrator system or to the display and reporting program to trigger creation of the waveform discussed above. In embodiments, the received data and generated reports may be stored in the one or more memory elements 16, for example. Otherwise, in embodiments, at step S5016, data from the next electrode may be received and validity may be determined for the data from the next electrode by returning to step S5008. Thereafter data may be collected and used to provide the ECG waveform or for any other purpose. As noted above, the test of FIG. 5, in embodiments, is performed when the device 10, including the monitor element 12 and pad 20 are placed on the patient's body but need not be repeated before every ECG procedure if they remain in place. In embodiments, the test of FIG. 5 may be repeated prior to every ECG procedure.

In embodiments, the monitor device 10 may be used for other applications. In embodiments, the monitor device 10 may be used to detect and report information regarding electrical activity of a fetal heart in a pregnant patient. Traditionally, fetal heartbeats are detected by manually placing and moving sensors on the pregnant woman's abdominal area—until a good signal is detected. This approach, however, is time consuming and may need to be repeated based on fetal movement. FIG. 7 illustrates an exemplary positioning of the ECG monitor device 10 on the abdomen of a pregnant patient. In this embodiment, an alternative electrode pad 120 may be used which has additional electrodes 126a, 126b, 126c . . . 126h along the continuous strip 120a on the abdomen of the patient. In embodiments there may be more or fewer additional electrodes as noted above. In embodiments, the monitor device 12 and electrode pad 120 may then be used to detect the electrical activity of the fetal heart based on monitoring of the electrodes.

Figure 6:
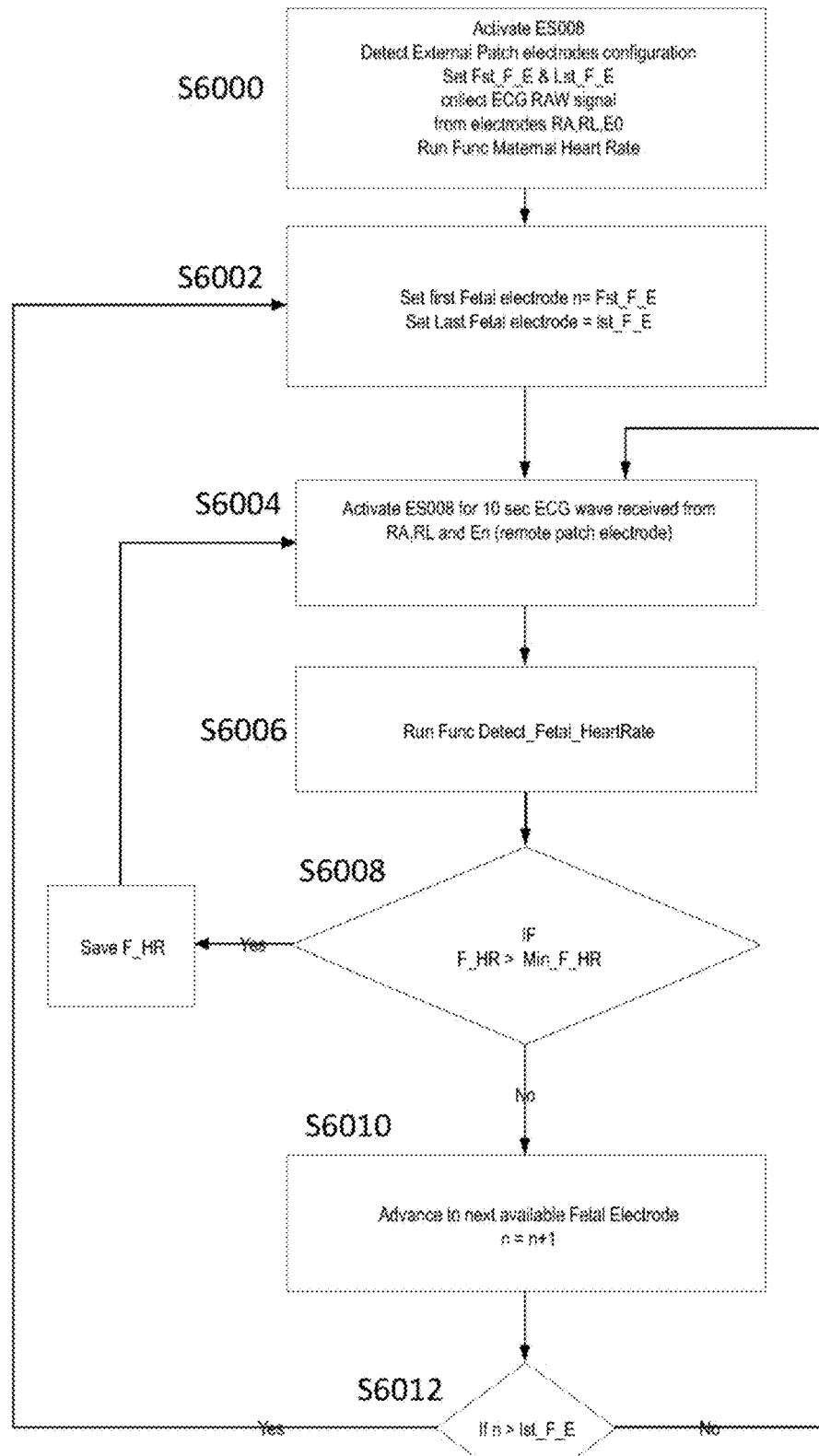
FIG. 6 illustrates an exemplary flow chart showing a method of detecting electrical activity associated with a fetal heart using the monitor device of FIG. 1 in accordance with an embodiment of the present disclosure.

FIG. 6 illustrates an exemplary flow chart showing a method of detecting electrical activity of a fetal heart using the monitor device 10. In embodiments, at step S6000, the monitor element 12 (ES008) may be activated in a manner similar to that described above with respect to step S5000. In embodiments the number of electrodes included in the pad 120 may be determined. In embodiments, the number of electrodes may be determined based on identification information provided from the OTP, for example. In embodiments, the number of electrodes may be input or provided by the administrator system and/or the mobile electronic device. In embodiments, at step S6002 the first electrode (Fst_F_E) and last electrode (Lst_F_E) may be designated and data may be collected from the electrodes. In embodiments, at step S6004, data is received from the electrodes 22, 24 as well as at least one of the electrodes 126a-126e on the continuous strip 120a. As noted above, a timing interval may be set to capture data from each of the electrodes. In embodiments, the electrodes 126a, 125b, 126c . . . 126h may be spaced at least 10 cm apart. In embodiments, the electrodes may be spaced further apart or closer together, for example, at the discretion of a clinician or health care worker. In embodiments, spacing between electrodes may vary based on the size of the pad 120 which may be selected based on the patient. In embodiments, at step S6006, the received data from the electrodes gathered in step S6004 is processed to identify electrical activity of the heart. In embodiments, at step S6008, identifying the electrical activity of the heart may include comparing the received data to a minimum threshold value. In embodiments, if the received data exceeds the threshold, the data may be stored as an indication of the fetal heart activity at step S6008a. Otherwise, in embodiments, at step S6010, data from the next electrode is collected based on a determination of whether there is another electrode to be analyzed at step S6012. In embodiments, this determination may be based on the number of electrodes included on the pad 120. In embodiments, if the current electrode is not the last electrode, the process returns to step S6004 to be repeated for the next electrode. Otherwise, in embodiments, the process returns to step S6002, where a new number of electrodes may be designated. Based on the information provided, in embodiments, the electrode that provides the best indication of the fetal heart activity may be identified. In embodiments, the data provided by most of the electrodes will not exceed the threshold which indicates that they are not receiving data indicative of electrical activity of the fetal heart. In embodiments, where more than one electrode provides data above the threshold, the data that is provided last is identified for monitoring the fetal heart. In the event that none of the electrodes provide data that exceeds the threshold a determination may be made that electrical activity of the fetal heart has not been detected.

In embodiments, a method for detecting electrical activity of a fetal heart using the ECG monitor device 10 may include: activating the ECG monitor element 12; identifying the electrodes provided on the electrode pad 120 including a first electrode and a last electrode; receiving first ECG data from the limb electrodes 22 and 24 and at least one electrode of the second group of electrodes 126a, 125b, 126c . . . 126h for a period of time (i.e. 10 s); analyzing the first ECG data to identify electrical activity of the fetal heart based on a threshold value; wherein, when the first ECG data exceeds the threshold value, it is stored and the step of receiving the first ECG data is repeated for the next electrode of the second group of electrodes, and when the first ECG data does not exceed the first threshold, the process moves on to identify the next second electrode and the step of receiving ECG data is repeated with respect to the next electrode; and determining whether ECG data from all electrodes has been analyzed. In embodiments, where ECG data associated with more than one electrode exceeds the threshold, the most recently analyzed electrode is designated as detecting the electrical activity of the fetal heart.

Figure 8:
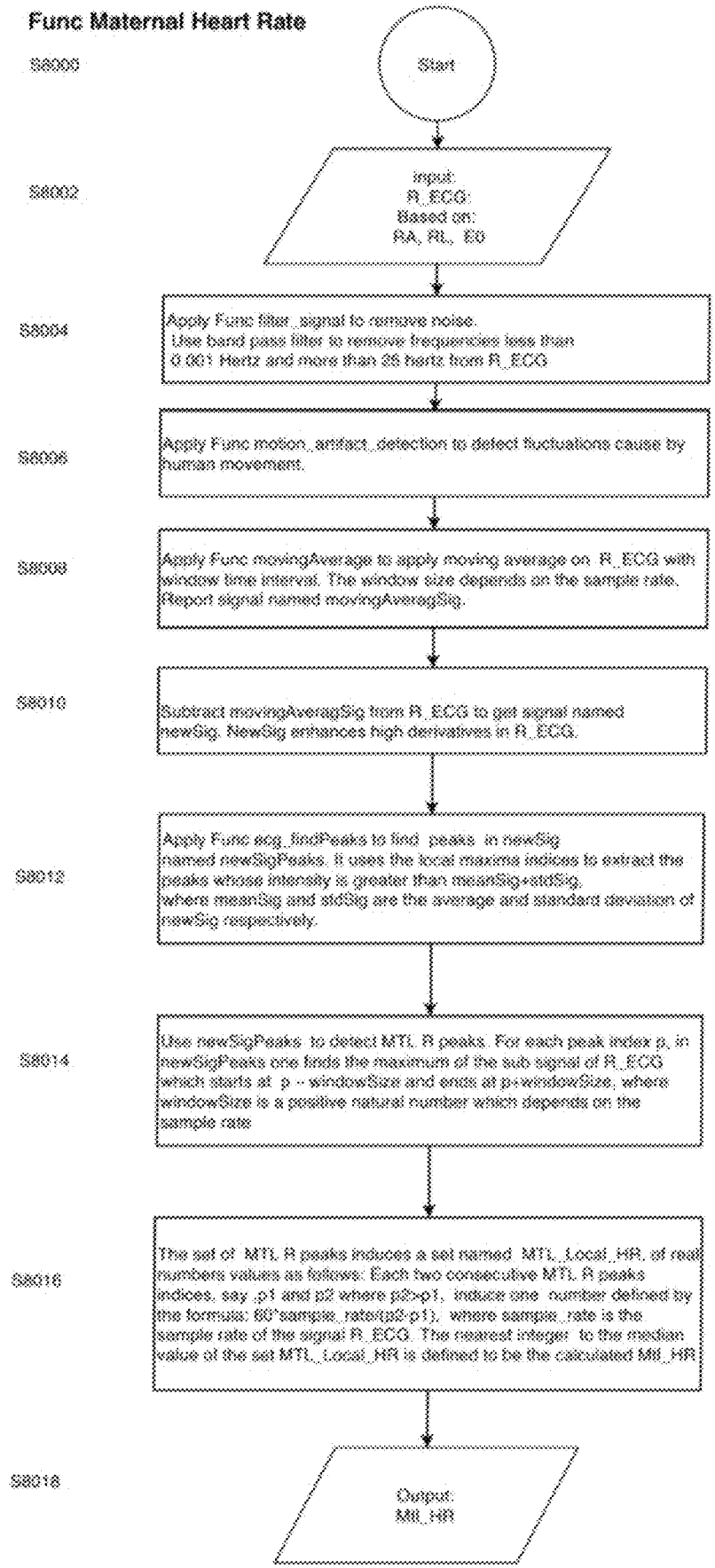
FIG. 8 is an exemplary flow chart showing a method of detecting electrical activity of a pregnant mother's heart using an ECG monitor device in accordance with an embodiment of the present disclosure.

In embodiments, the ECG monitor device 10 may also be used to detect electrical activity of a mother's heart. FIG. 8 illustrates an exemplary flow chart for detecting a pregnant mother's heartbeat, or more specifically, electrical activity of the mother's heart. In embodiments, the process starts at step S8000 in which the device 10 may be activated. In embodiments, at step S8002, data from each of the electrodes 22, 24 and 126a, 126b, 126c . . . 126h may be captured in the manner described above, for example and provided as an input data signal R_ECG. In embodiments, at step S8004, the data may be filtered using a band pass filter to eliminate noise. In embodiments, the signal to noise ratio may be increased using a moving average calculation on the received signal to remove noise with high frequencies. In embodiments, different approaches may be used to analyze the received signal. In embodiments, band pass filters may be used to filter noise out of the signal. In embodiments, a low pass filter and a high pass filter may be used together to clean the data stream or signal. In embodiments, a finite impulse response (FIR) bandpass filer may be used to filter noise from the received signal. In embodiments, filtering may be provided between 0.0001 Hz and 25 Hz, for example. In embodiments, various filter types may be used including Butterworth, Chebyshev, Elliptic and Bessel, to name a few. In embodiments, the band pass filtering may eliminate frequencies below 0.001 Hz and more than 25 Hz. In embodiments, at step S8006, processing may be performed to detect whether the patient has moved. In embodiments, a patient movement function may be applied to the data stream or signal to detect artifacts in the data caused by patient movement. In embodiments, patient movement may be determined based on information provided by an accelerometer or other motion sensing device that may be mounted on or in the monitor element 12. In embodiments, data from this monitor element 12 or sensor may be continuously sampled and data captured may be evaluated based on body position and/or movement to determine signal quality or relevance to the test needed. In embodiments, at step S8008, a moving average may be determined based on the data signal to remove the effect of patient movement. In embodiments, this step may be used to remove the effect of human movement (even small movements not associated with walking or running) to increase the quality of data signal. In embodiments, at step S8010 the moving average is subtracted from the data signal to determine the variation based on the patient movement to provide a "newsignal." In embodiments, at step S8012, the newsignal may be processed to identify peaks above a determined threshold. As illustrated a find peak function may be applied to the newsignal in order to provide a peak newsig signal in which peaks in the new signal are identified. In embodiments, at step S8014, the peak newsig signal may be processed to detect peaks as indicate in FIG. 8 for example. At steps S8016, the mother's heartbeat signal indicating electrical activity of the other's heart may be provided based on the detected peaks from step S8014. In embodiments, the mother's heartbeat signal may be output in step S8018. In embodiments, at step S8018, the mother's heartbeat signal may be recorded and/or transmitted to the administrator system, central station or mobile electronic device.

Now that embodiments of the present invention have been shown and described in detail, various modifications and improvements thereon can become readily apparent to those skilled in the art. Accordingly, the exemplary embodiments of the present invention, as set forth above, are intended to be illustrative, not limiting. The spirit and scope of the present invention is to be construed broadly.

What is claimed is:

1. An ECG monitor device comprising:
an ECG monitor element including:
a processor;
a memory element operatively connected to the processor, the memory element including executable instructions to process ECG data to provide an ECG waveform;
a power source;
an analog interface operatively connected to the processor; and
a communication element operatively connected to the processor and the memory element and configured to send and receive data; and
an electrode pad connected to the ECG monitor element including:
a first group of electrodes positioned on a base of the electrode pad and directly connected to the analog interface;
a second group of electrodes positioned on a continuous strip extending away from the base, wherein the continuous strip is stretchable relative to the base;
a multiplexer mounted on the electrode pad and connected to the analog interface, wherein the second group of electrodes is connected to the multiplexor and the multiplexor is operable to selectively provide data from each electrode of the second group of electrodes to the ECG monitor element;
wherein the processor processes data from the first group of electrodes and the second group of electrodes to provide electrocardiogram information sufficient to selectively provide an ECG waveform consistent with a single lead electrode and a multiple lead ECG.

2. The ECG monitor device of claim 1, further comprising a connector element electrically connecting the monitor element to the electrode pad.

3. The ECG monitor device of claim 2, wherein the connector element is a magnetic element configured to securely connect the monitor element to the electrode pad.

4. The ECG monitor device of claim 2, wherein the processor provides control information to the multiplexer associated with sampling of data provided by the second group of electrodes.

5. The ECG monitor device of claim 4, wherein the control information indicates a sampling time interval and sampling duration.

6. The ECG monitor device of claim 4, wherein the electrode pad further comprises a pad memory element including identification information associated with a configuration of the electrodes on the electrode pad.

7. The ECG monitor device of claim 6, wherein the processor receives the identification information from the pad memory and the control information is based on the identification information.

8. The ECG monitor device of claim 1, wherein the processor processes data provided from the first group of electrodes and the second group of electrodes to provide the electrocardiogram information.

9. The ECG monitor device of claim 8, wherein the processing includes determining electrode input information associated with a respective electrode that provided a first portion of the data.

10. The ECG monitor device of claim 9, wherein the processing includes analyzing a time stamp, a sampling interval and a sampling determination to determine the electrode input information.

11. The ECG monitor device of claim 8, wherein the electrode input information is stored in the memory and used to construct the ECG waveform.

12. A method of testing the ECG monitor device of claim 1, comprising:
activating the ECG monitor device of claim 1;
receiving, at the ECG monitor device from the electrode pad, test identification information associated with the test to be performed including duration information;
determining, by the ECG monitor device, a configuration of the electrode pad;
determining, by the ECG monitor device, timing information for data capture of data provided by the electrode pad based at least on the configuration of the electrode pad;
receiving, by the ECG monitor device from the electrode pad, first electrode data;
determining, by the ECG monitor device, that the first electrode data is valid;
wherein, when the first electrode data is invalid, an invalid message is generated and stored in the memory; and
otherwise, a valid message is generated and stored in the memory with the first electrode data;
determining, by the ECG monitor device, whether valid electrode data has been provided from all electrodes;
wherein, when valid data has not been received from all electrodes, the receiving step and determining steps are repeated for second electrode data; and
otherwise, a test complete report is generated and saved in memory to indicate that the test has been completed.

13. The method of claim 12, wherein the step of determining the configuration of the electrode pad is based on the test identification information.

14. The method of claim 12, wherein the step of determining the configuration of the electrode pad includes comparing the test identification information to stored identification information included in the memory.

15. The method of claim 12, wherein the step of determining the configuration of the electrode pad includes receiving instructions via the communication element.

16. The method of claim 12, wherein the timing information is determined based on the configuration of the electrode pad and a number of leads to be used in providing the ECG waveform.

17. The method of claim 12, wherein the step of determining that the first electrode data is valid is based on noise to signal ratio of the signal including the first electrode data.

18. The method of claim 12, wherein the step of determining that the first electrode data is valid is based on a percentage of detected peaks in the signal including the first electrode data.

19. The method of claim 12, wherein the step of determining that the first electrode data is valid is based on an anticipated wave pattern associated with the electrode pad.

20. The method of claim 12, wherein the test complete report is transmitted to an administrator computer system using the communication element.

* * * * *